US009764097B2

(12) United States Patent
Perot et al.

(10) Patent No.: US 9,764,097 B2
(45) Date of Patent: Sep. 19, 2017

(54) NEEDLE ASSEMBLY AND INJECTION DEVICE WITH FOLDABLE NEEDLE PROTECTING MEANS

(75) Inventors: Frederic Perot, Saint-Paul-de-Varces (FR); Guillaume Grunhut, Grenoble (FR); Adrien Plouvier, Saint-Martin-d'Heres (FR)

(73) Assignee: Becton Dickinson France, Le Pont de Claix (FR)

( * ) Notice: Subject to any disclaimer, the term of this patent is extended or adjusted under 35 U.S.C. 154(b) by 799 days.

(21) Appl. No.: 14/110,851

(22) PCT Filed: Apr. 10, 2012

(86) PCT No.: PCT/EP2012/001544
§ 371 (c)(1),
(2), (4) Date: Oct. 9, 2013

(87) PCT Pub. No.: WO2012/139745
PCT Pub. Date: Oct. 18, 2012

(65) Prior Publication Data
US 2014/0039408 A1 Feb. 6, 2014

(30) Foreign Application Priority Data
Apr. 11, 2011 (EP) ..................................... 11305423

(51) Int. Cl.
*A61M 5/32* (2006.01)
(52) U.S. Cl.
CPC .......... *A61M 5/3275* (2013.01); *A61M 5/326* (2013.01); *A61M 5/3287* (2013.01);
(Continued)

(58) Field of Classification Search
CPC ...... A61M 5/32; A61M 5/3275; A61M 5/326; A61M 5/3287; A61M 2205/583; A61M 5/3257; A61M 5/3247; A61M 2005/3267; A61M 2005/583; A51M 2005/3247; A51M 2005/3267
(Continued)

(56) References Cited

U.S. PATENT DOCUMENTS

| 5,201,708 A | 4/1993 | Martin |
| 5,487,733 A | 1/1996 | Caizza et al. |

(Continued)

FOREIGN PATENT DOCUMENTS

| JP | 2-26563 A | 1/1990 |
| WO | 2009/144546 A1 | 12/2009 |

*Primary Examiner* — Kevin C Sirmons
*Assistant Examiner* — Tiffany Legette-Thompson
(74) *Attorney, Agent, or Firm* — The Webb Law Firm

(57) ABSTRACT

The present invention relates to a needle including: a needle hub having a needle with a distal tip; a ring for protecting the needle in one of a storage condition or end-of-use condition of the needle assembly; a foldable element for moving the protective ring; a biasing element for urging the foldable element from its folded configuration to an unfolded configuration; a retainer for maintaining the biasing element in an intermediate stressed state at least in the storage condition of the needle assembly; and a deactivating element for releasing said retainer at least at the end of the injection step. The invention also relates to an injection device including such a needle assembly and a container.

21 Claims, 7 Drawing Sheets

(52) U.S. Cl.
CPC ............ *A61M 2005/3247* (2013.01); *A61M 2005/3267* (2013.01); *A61M 2205/583* (2013.01)

(58) Field of Classification Search
USPC ........................................ 604/198, 192, 263
See application file for complete search history.

(56) References Cited

U.S. PATENT DOCUMENTS

| | | | |
|---|---|---|---|
| 5,591,138 A | | 1/1997 | Vaillancourt |
| 5,607,400 A | * | 3/1997 | Thibault ........... A61M 5/31513 604/218 |
| 6,171,284 B1 | | 1/2001 | Kao et al. |
| 6,986,759 B1 | | 1/2006 | Jeremijevic |
| 8,460,241 B2 | | 6/2013 | Grimard |
| 2002/0165498 A1 | | 11/2002 | Ward |
| 2003/0004465 A1 | * | 1/2003 | Ferguson ............. A61B 5/1433 604/198 |
| 2004/0044318 A1 | * | 3/2004 | Fiser .................. A61M 5/3275 604/263 |
| 2005/0059936 A1 | | 3/2005 | Fiser et al. |
| 2008/0051724 A1 | * | 2/2008 | Bedford ............. A61M 5/3275 604/192 |

\* cited by examiner

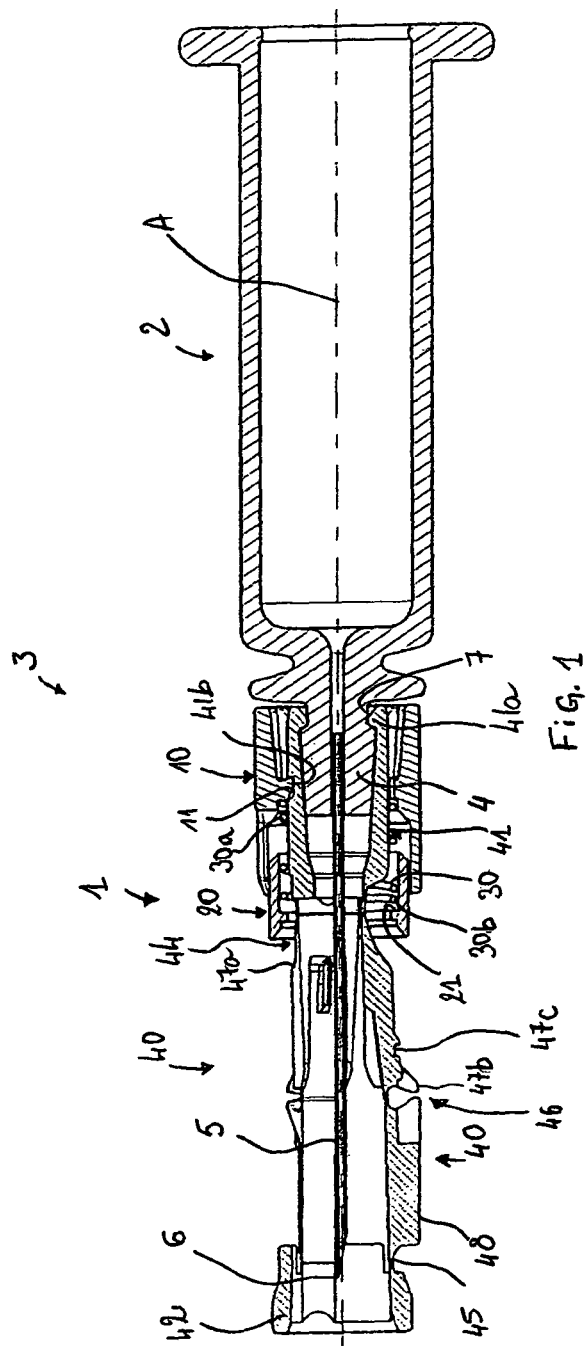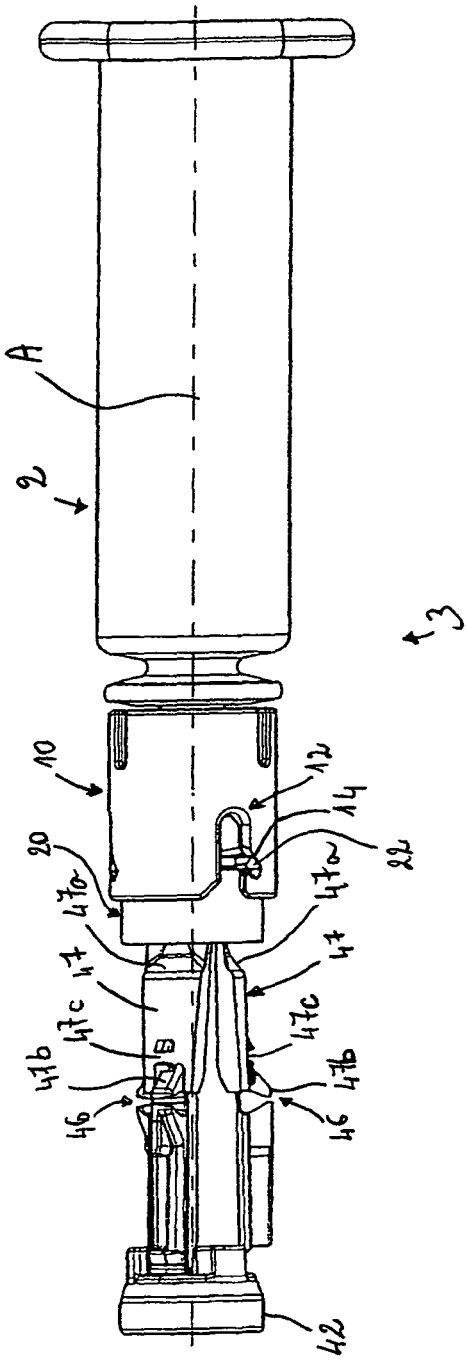

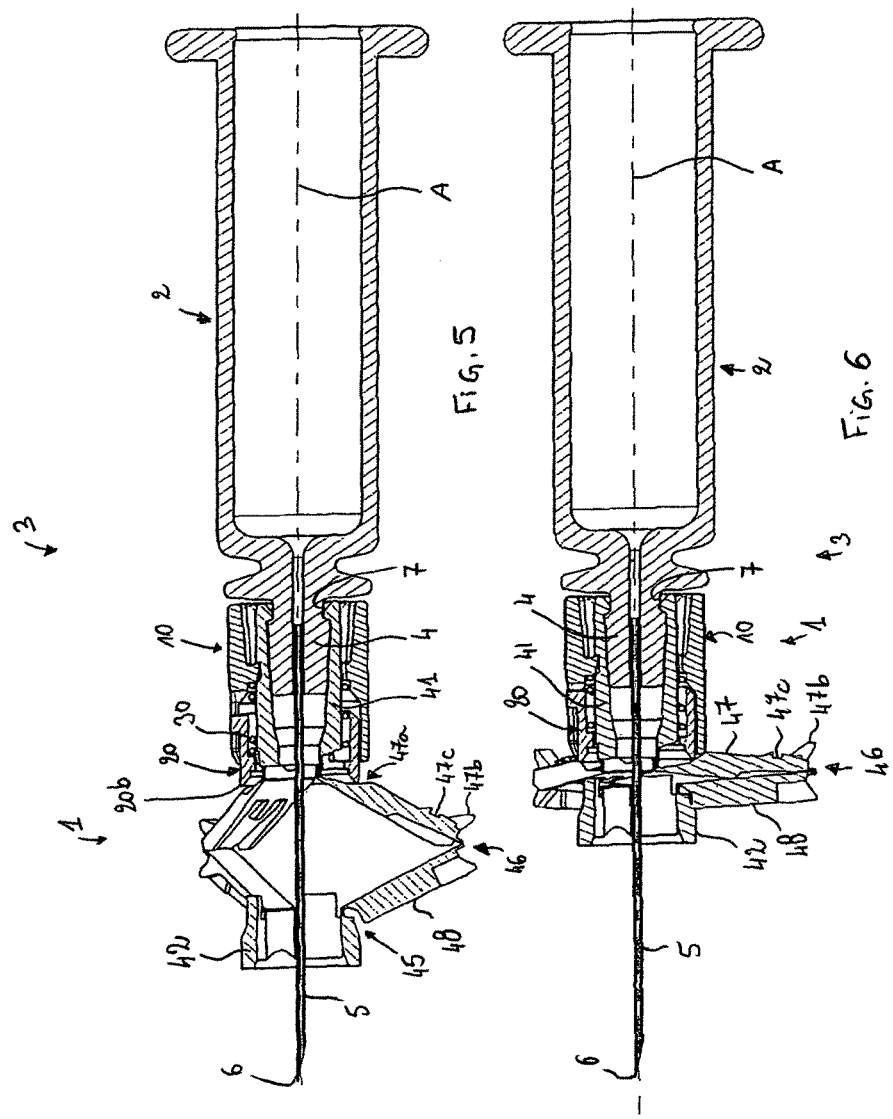

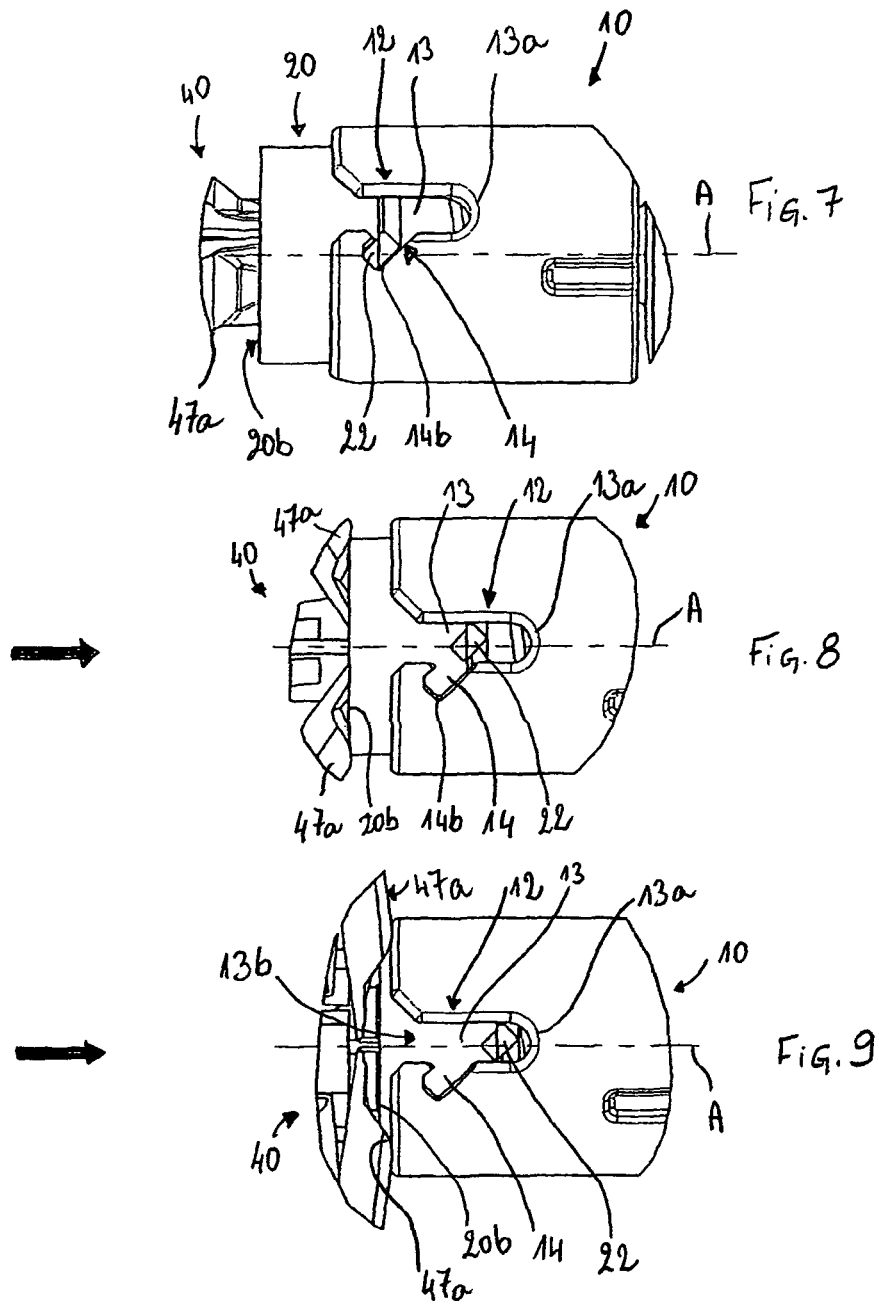

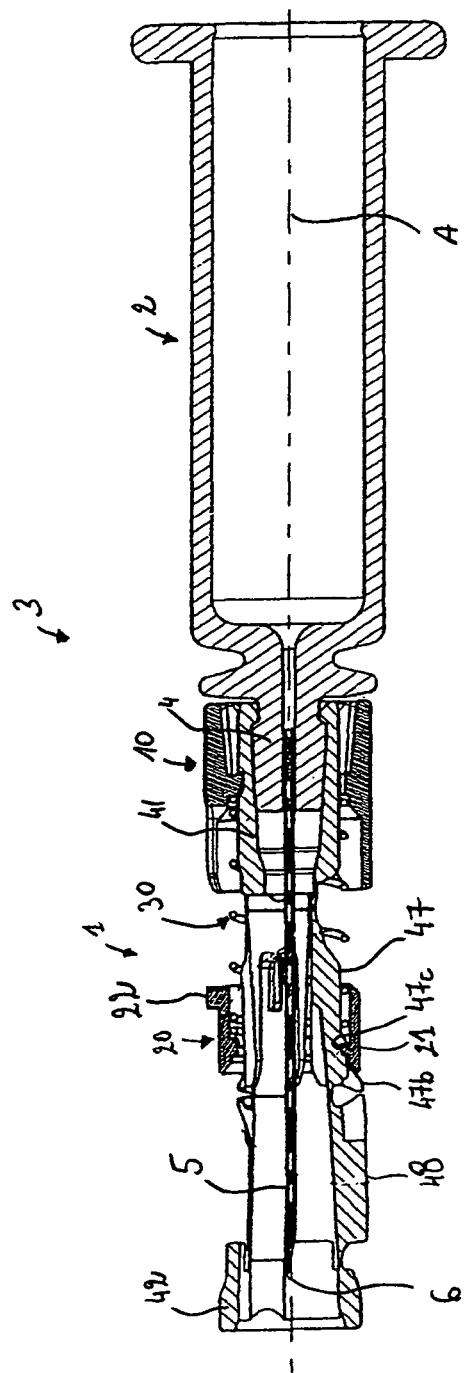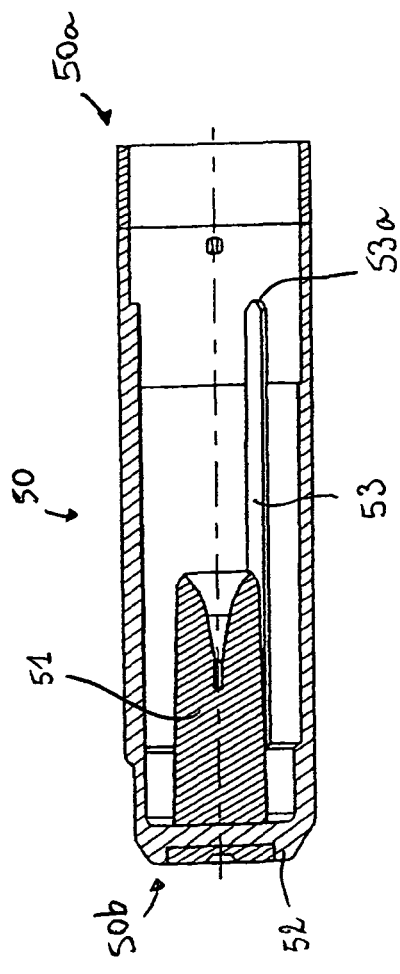
Fig. 13
Fig. 14

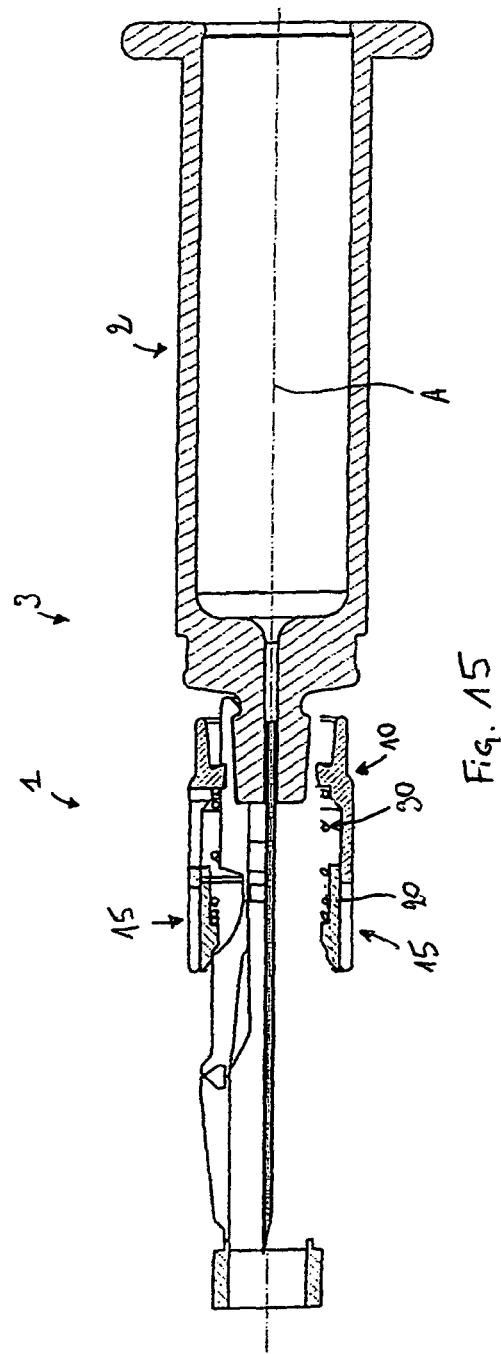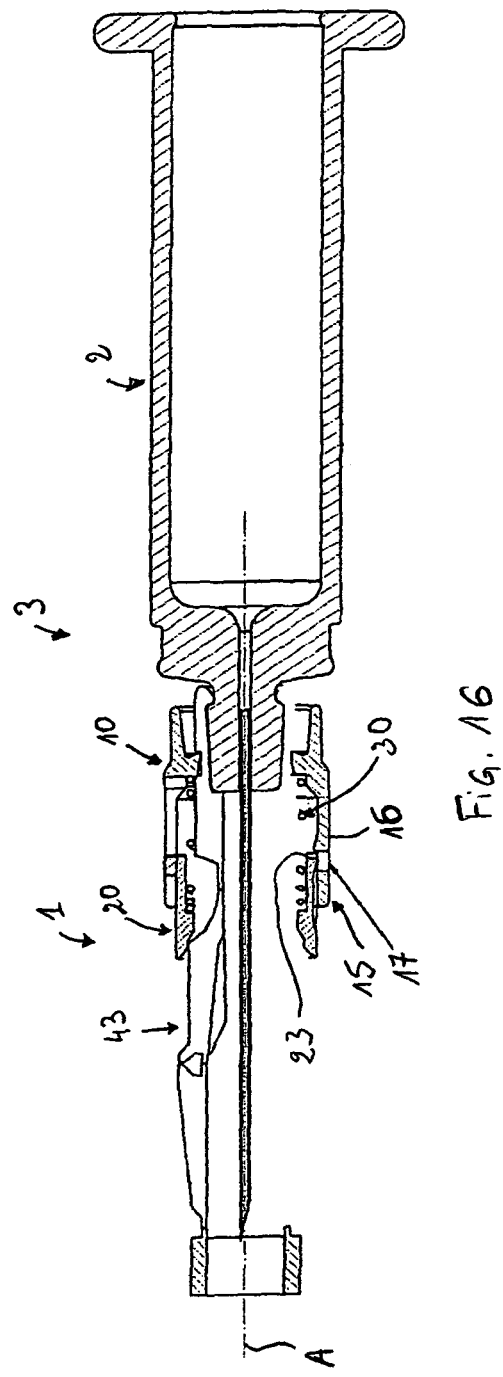

NEEDLE ASSEMBLY AND INJECTION DEVICE WITH FOLDABLE NEEDLE PROTECTING MEANS

BACKGROUND OF THE INVENTION

Field of the Invention

The present invention relates to a needle assembly for an injection device, in particular a needle assembly to be used in combination with a container comprising a product to be injected, said needle assembly comprising a safety system for protecting the needle before and after use, the needle assembly allowing obtaining a very compact injection device.

Description of Related Art

In this application, the distal end of an element or of a device means the end furthest away from the hand of the user and the proximal end means the end closest to the hand of the user, when the element or device is in the use position. Similarly, in this application, the terms "in the distal direction" and "distally" mean in the direction of the injection, and the terms "in the proximal direction" and "proximally" mean in the direction opposite to the direction of injection.

In this application, the terms "radially", "outwardly" and "inwardly" are intended to mean radially, outwardly and inwardly with respect to the longitudinal axis of the needle assembly and injection device of the invention.

Injection devices, such as syringes, are well known. Many different types of injection devices have been designed for administering medicines. Injection devices usually comprise a container intended to receive the product to be injected and a plunger rod intended to move a stopper within the container so as to expel the product therefrom at the time of injection. Empty and pre-filled disposable injection devices exist but prefilled devices are now preferred because they are convenient, safe and efficient and may be used directly in emergency cases.

Usually, in addition to these elements, it is preferred that the injection device further comprises a safety system for protecting the needle, and in particular for protecting its distal sharp tip, before and after use of the injection device, in other words before the injection and after the injection. It is also preferred that such safety system be triggered automatically after the end of the injection, with no additional operation required from the user, in order to ensure the safety of said user. Safety systems usually are provided under the form of sleeves intended to cover the needle at the end of injection, the presence of such sleeves usually increasing the volume and the overall length of the injection device.

Moreover, prefilled injections devices are usually filled by a pharmaceutical company, packaged for use, and then typically stored at a doctor's office, hospital, etc. until they are needed for use. In such conditions, the prefilled injection device occupies a predetermined amount of storage space based upon the size of the injection device (typically comprising a syringe barrel, a stopper, a plunger rod, and possibly a needle, and a safety system). In some cases, the predetermined amount of storage space the injection device will occupy is a maximum space approximating the length of the plunger rod, plus the length of the syringe barrel, plus the length of the needle (if provided).

Required storage space is an important feature for prefilled injection devices. It is especially important when the medicine contained in these devices must be stored and transported at low temperatures. Storage of these injection devices may require refrigeration and can be expensive. This is especially the case in hospitals and pharmacies, where storage space for medicines is limited.

Thus, there is a need for an injection device which would be particularly compact, particularly when the injection device is prefilled, and that would nevertheless protect the user from accidental needlestick injuries before use and after use. There is therefore still a need for a needle assembly comprising a safety system, said needle assembly requiring less space as possible.

Moreover, such an injection device must be simple to use, and preferably would not alter the typical process followed by the medical staff when administering an injection.

SUMMARY OF THE INVENTION

An aspect of the present invention is therefore a needle assembly for use with a container, comprising:
  i) a needle hub having a needle fixed thereon, said needle having a distal tip, and
  ii) a needle safety system comprising:
    a protective ring capable of moving in translation with respect to said needle hub between a distal position, in which said protective ring surrounds at least the distal tip of said needle and in which said needle assembly is in one of a storage condition or end-of-use condition, and a proximal position, in which said protective ring leaves said distal tip uncovered and wherein said needle assembly is in a use condition, said protective ring being movable in said proximal position between intermediate positions in which the needle is partially inserted into an injection site and a most proximal position, in which the needle is fully inserted into said injection site,
    foldable means coupled to said protective ring and to said needle hub, capable of going from an unfolded configuration, in which said protective ring is in its distal position, to a fully folded configuration, in which said protective ring is in its most proximal position,
    biasing means capable of expanding from a stressed state to a rest state for urging said foldable means from their folded configuration to their unfolded configuration when the needle is removed from the injection site,
    retaining means for maintaining said biasing means in an intermediate stressed state at least in the storage condition of the needle assembly,
    deactivating means for releasing said retaining means during the insertion step of the needle.

Another aspect of the invention is an injection device comprising a needle assembly as described herein, further comprising a container intended to be filled or filled with a product to be injected via said needle, said needle hub being fixed to a distal end of said container. In embodiments, said needle hub and said container may be one single element.

By "foldable means" is meant according to the present application, means capable of going from an unfolded configuration to a folded configuration, so that the overall length of said foldable means, measured along a determined axis of said foldable means, is reduced when said foldable means go from said unfolded configuration to said folded configuration.

The needle assembly of the invention occupies limited space, even in its storage condition. The needle assembly of the invention allows obtaining injection devices which occupy little space, even if the injection device is prefilled with the product to be injected. The needle assembly and/or injection device of the invention are therefore easy to store in a compact way. In addition, the safety system of the needle assembly and injection device of the invention is automatically triggered at the end of the injection step when the needle is removed from the injection site, with no additional step required from the user, other than simply withdrawing the injection device from the injection site or in case of a misuse of the injection device.

In embodiments, the needle assembly further comprises locking means for maintaining said foldable means in their unfolded configuration in the end-of-use condition of said needle assembly. Such embodiments allow obtaining very safe injection devices, where the risk of accidental needle stick injuries after use is very limited.

In embodiments, said safety system comprises at least a mobile ring, coupled to said needle hub by said biasing means, said mobile ring being movable in translation with respect to said needle hub between a proximal position, in which said mobile ring is limitedly mobile in translation and in rotation with respect to said needle hub and forms at least part of said retaining means and deactivating means, and a distal position, in which said mobile ring forms at least part of said locking means.

For example, the mobile ring forms part of said locking means by preventing a user from manually trying to fold again the foldable means in a view of using the needle assembly again.

The presence of at least a mobile ring as part of the locking means as described above allows the locking means to be both automatically triggered and particularly safe: indeed, thanks to the safety system of the needle assembly of the invention, no additional step is required from the user in order to trigger the locking means and the user has no way of unlocking said locking means in the end-of-use condition of the needle assembly.

In embodiments, said safety system comprises:
a fixed ring at least partially receiving said needle hub, and fixed in translation with respect to said needle hub,
a mobile ring, coupled to said fixed ring by said biasing means, and capable of being at least partially received within said fixed ring, said mobile ring being movable in translation with respect to said fixed ring between a proximal position, in which said mobile ring is limitedly mobile in translation and in rotation with respect to said fixed ring and forms at least part of said retaining means and deactivating means, and a distal position, in which said mobile ring forms at least part of said locking means.

In embodiments, said fixed ring being provided with a proximal radial abutment surface and said mobile ring being provided with a distal radial abutment surface, said biasing means being a helical spring located between said fixed ring and said mobile ring so that the distal end of said helical spring bears on said distal radial abutment surface and the proximal end of said helical spring bears on the proximal radial abutment surface, said retaining means comprise at least a cam provided with a recess, said cam being located on one of said fixed ring and mobile ring, and at least a peg located on the other one of said fixed ring and mobile ring, said peg being capable of moving within said cam between a locked state in which said needle assembly is in its storage condition and said peg is engaged in said recess, said helical spring being in its intermediate stressed state, and a free state in which said peg is disengaged from said recess after activation of said deactivating means, said needle assembly being then in one of its use or end-of-use conditions.

In embodiments, at least part of said deactivating means being located on said foldable means, said deactivating means are activated when said foldable means leave their unfolded configuration to reach their fully folded configuration.

In embodiments, said foldable means comprises at least one leg having a proximal end pivotally coupled to said needle hub, and a distal end pivotally coupled to said protective ring, said leg being provided with a hinge dividing a length of said leg in a proximal segment and a distal segment, said proximal and distal segments being aligned on each other and parallel to said needle in the unfolded configuration of said foldable means, said proximal and distal segments pivoting around said hinge and extending radially outwardly in the fully folded configuration of said foldable means.

In embodiments, said foldable means comprise at least two of such legs, opposite each other with respect to said needle.

In other embodiments, said foldable means comprise at least three such legs, said three legs being regularly angularly distributed around said needle. Such embodiments provide for an improved stability of the foldable means, especially in their unfolded configuration. The safety of the needle assembly after use is therefore improved.

In embodiments, said cam being located on said fixed ring, said cam comprising a longitudinal track open at its distal end and closed at its proximal end, and a side track extending circumferentially and distally from a point of said longitudinal cam to a closed end, said closed ended side track forming said recess, said peg is located on said mobile ring and is disengageable from said closed ended side track by proximal translation and rotation of said mobile ring with respect to said fixed ring, said deactivating means comprise at least a part of said proximal segment(s), said part of said proximal segment(s) coming in abutment on a distal end of said mobile ring when said foldable means go from their unfolded configuration to their fully folded configuration and said proximal segment(s) extend radially outwardly, said part of proximal segment(s) thereby pushing said mobile ring in the proximal direction, the movement of said peg in said side track thereby causing rotation of said mobile ring with respect to said fixed ring, thus disengaging said peg from said recess of said cam.

In embodiments, said retaining means comprise three such cams and pegs, each cam cooperating with a corresponding peg, said cams being regularly angularly distributed along a circumference of said fixed ring, said corresponding pegs being regularly angularly distributed along a circumference of said mobile ring. Such embodiments allow for an improved stability and efficiency of the safety system.

In embodiments, said locking means comprise a groove located in a distal area of an outer wall of said proximal segment, and a radial rim located on an inner wall of said mobile ring, said radial rim being engaged in said groove in the end-of-use condition of said needle assembly, so as to prevent said hinge from allowing said proximal segment to pivot with respect to said distal segment. A double lock system is thereby provided as not only the foldable means may not be folded again, but the mobile ring itself may not be removed from its position. The needle assembly is therefore particularly safe and accidental needlestick injuries after use are prevented.

In embodiments, the needle assembly further comprises protection means for preventing access to the biasing means in the end of use condition of the needle assembly. For example, the fixed ring may be further provided with tongues extending in the proximal direction, said tongues surrounding the helical spring in its rest state. Such embodiments prevent access to the helical spring and therefore prevent any unlocking of the needle assembly from an end-of use condition to a storage condition.

In embodiments, the needle assembly further comprises a protective cap intended to be mounted on said needle assembly when said needle assembly is in its storage condition, said protective cap being dimensioned so as to surround said needle assembly when it is mounted on said needle assembly.

In embodiments, said protective cap comprises an elastomeric part extending proximally from an inner face of a distal transversal wall of said cap, said r elastomeric part being received within said protective ring and receiving the distal tip of said needle when said protective cap is mounted on said needle assembly.

The protective cap may further comprise securing means for preventing said biasing means to be accidentally triggered during storage of said needle assembly inside said protective cap. For example, the inner wall of said protective cap is provided with at least a longitudinal ridge, said longitudinal ridge being engaged in at least one of said longitudinal track of said cam(s) when said protective cap is mounted on said needle assembly, said longitudinal ridge thereby preventing the corresponding peg from escaping from the recess formed by the closed ended side track in which said peg is engaged.

BRIEF DESCRIPTION OF THE DRAWINGS

The present invention will now be described in greater detail based on the following description and the appended drawings in which:

FIG. 1 is a cross section view of an embodiment of a needle assembly and injection device of the invention, in a before use or storage condition, FIG. 2 is a side view of the needle assembly and injection device of FIG. 1, FIG. 5 is a cross section view of the needle assembly and injection device of FIG. 1 in the use condition during the insertion step of the needle, FIG. 6 is a cross section view of the device of FIG. 5 in the use condition, when the needle is fully inserted and where injection step may take place, FIG. 7 is a partial side view of the device of FIG. 1, FIG. 8 is a partial side view of the device of FIG. 1 when it is in the use condition shown on FIG. 5, FIG. 9 is a partial side view of the device of FIG. 1 when it is in the use condition shown on FIG. 6, FIG. 13 is a cross section view of the needle assembly and injection device of FIG. 1 when it is in the end-of-use condition, FIG. 14 is a cross section of an embodiment of a protective cap for the needle assembly of FIG. 1, FIG. 15 is a cross section view of another embodiment of a needle assembly and injection device of the invention in the end of use condition, FIG. 16 is a cross section view of the embodiment of FIG. 12 in the end-of-use condition of the needle assembly.

With reference to FIG. 1 is shown a needle assembly 1 of the invention in combination with a container 2 intended to receive a product to be injected, thereby forming an injection device 3 of the invention.

DESCRIPTION OF THE INVENTION

Figure 3:
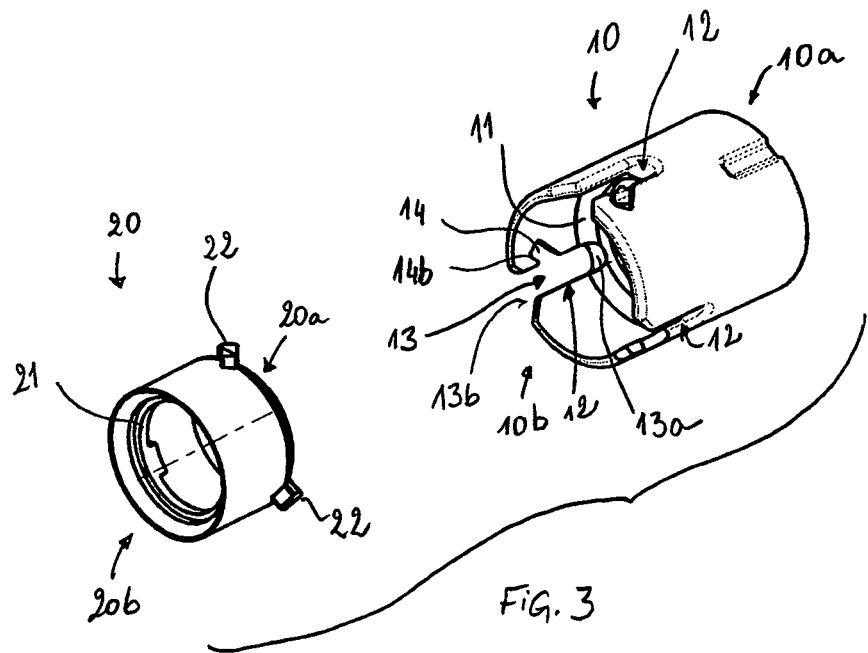
FIG. 3 is a perspective exploded view of the fixed ring and mobile ring of the needle assembly of FIG. 1.

The container 2 shown on FIG. 1 is a syringe but it also could be a cartridge, a pen.

The needle assembly 1 and the injection device of the invention have a common longitudinal axis A. The needle assembly 1 comprises a needle hub 4 having a needle 5 fixed thereon, said needle 5 having a free distal tip 6. The needle hub 4 is further provided in its proximal region with a circular groove 7. In the embodiment shown on the Figures of the present application, the needle hub 4 of the needle assembly 1 is a part of the distal end of the container 2. In embodiments not shown, the needle hub is an element distinct from the container which is fixed and/or connected to the distal end of the container by any classical fixing means, such as gluing, screwing, interlocking, etc. . . . In such case, the needle 5 can be a standard needle with one free distal tip 6 but it also can have two sharps ends.

The needle assembly 1 comprises a needle safety system for protecting the needle 5, in particular the distal tip 6 of the needle 5, at least in a storage condition of the needle assembly 1 as shown on FIG. 1 and in an end-of-use condition (see FIG. 13) of said needle assembly 1 after an injection step has been performed and the needle 5 has been removed from the injection site (not shown), in order to prevent accidental needlestick injuries for the user. With reference to FIG. 1, the needle safety system comprises a fixed ring 10, which is fixed in translation with respect to the needle hub 4, a mobile ring 20, which is movable in translation with respect to the needle hub 4, a helical spring 30 coupling together the fixed ring 10 and the mobile ring 20, and a foldable member 40. The mobile ring 20 is therefore coupled to the needle hub 4 by the helical spring 30, in the example shown through the intermediate of the fixed ring 10. In embodiments not shown, the fixed ring may not be present and the safety system could comprise only the mobile ring 20 which would be directly coupled to the needle hub 4.

When present, the fixed ring 10 allows tight and fixed positioning of the needle assembly 1 on the needle hub 4.

With reference to FIG. 3, the fixed ring 10 and the mobile ring 20 will now be described in details. The fixed ring 10 has the global shape of a portion of a tube having a proximal end 10a and a distal end 10b, and is provided on its inner wall with a proximal radial abutment surface formed of a circular ridge 11. On the example shown, the wall of the fixed ring 10 is further provided with three cams 12 regularly angularly distributed along a circumference of the fixed ring 10. In embodiments not shown, the fixed ring 10 could be provided with a single cam or with two cams diametrically opposed. Alternatively, the fixed ring 10 could be provided with four or more cams. Each cam 12 comprises a longitudinal track 13 open at its distal end 13b, at the location where it rejoins the distal end 10b of the fixed ring 10, and closed at its proximal end 13a. Each cam 12 further comprises a side track 14, extending circumferentially and distally from a point of the longitudinal track 13. The side track 14 is closed at its distal end 14b, thereby forming a recess.

Still with reference to FIG. 3, the mobile ring 20 has also the global shape of a portion of a tube having a proximal end 20a and a distal end 20b, said mobile ring 20 being dimensioned so as to be able to be at least partially received within said fixed ring 10. The mobile ring 20 is provided on its inner wall with a distal radial abutment surface under the form of a circular ridge 21. As appears from FIG. 1, the helical spring 30 is intended to couple the fixed ring 10 to the mobile ring 20, by having its proximal end 30a bearing on the proximal radial abutment formed by the circular ridge 11 of the fixed ring 10 and having its distal end 30b bearing on the distal radial abutment surface formed by the circular ridge 21 of the mobile ring 20.

The mobile ring 20 is further provided on its outer wall with three pegs 22 (two only are visible on FIG. 3) regularly angularly distributed along a circumference of the mobile ring 20 and capable of being received within the corresponding cams 12, so as to cooperate with said cams 12, in order to either retain the mobile ring 20 in a proximal position with respect to said fixed ring 10 or on the contrary to move said mobile ring 20 to a distal position with respect to said fixed ring 10, in combination with the helical spring 30. Like for the cams 12, the number of pegs 22 could vary between 1 and 4 or more.

Figure 4:
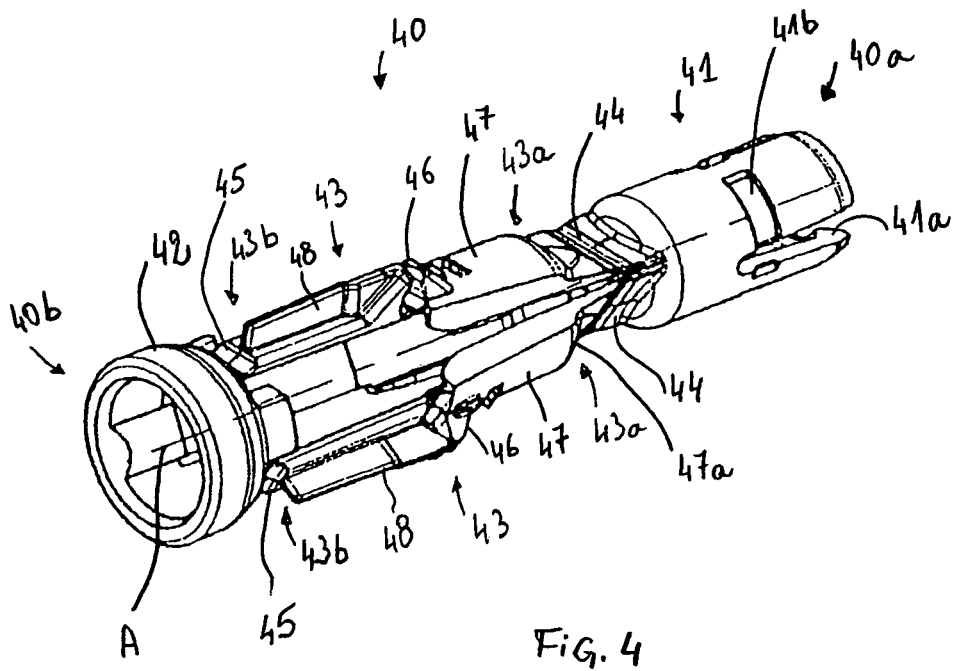
FIG. 4 is a perspective view of the foldable means of the needle assembly of FIG. 1.
Figure 10:
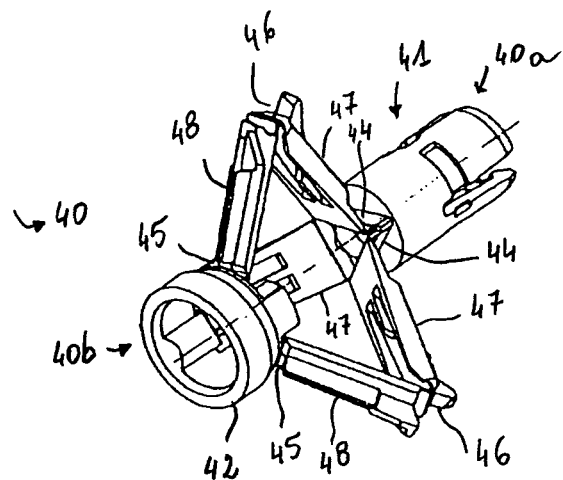
FIG. 10 is a perspective view of the foldable means of the device of FIG. 1 when it is in the condition shown on FIG. 5.
Figure 11:
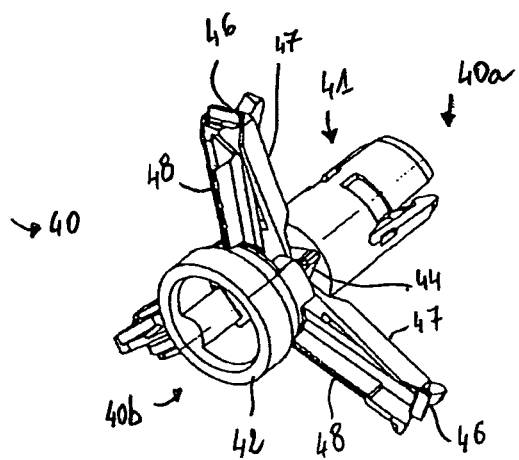
FIG. 11 is a perspective view of the foldable means of the device of FIG. 1 when it is in the condition shown on FIG. 6.

With reference to FIGS. 4 and 10-11, the foldable member 40 will now be described in details. The foldable member 40 has a globally elongated shape with a proximal end 40a and a distal end 40b, and having a longitudinal axis A corresponding to the longitudinal axis of the needle assembly 1. It is provided in its proximal region with a tubular portion 41. The tubular portion 41 is provided with a proximal inner rim 41a at its proximal end. The tubular portion 41 is further provided on its outer wall with a window 41b.

The foldable member 40 is further provided at its distal end 40b with a protective ring 42, intended to protect the distal tip 6 of the needle 5 in the storage and end-of-use conditions of the needle assembly 1 of the invention, as will appear from the description below.

With reference to FIGS. 4 and 10-11, the foldable member 40 is further provided with three legs 43 located between the tubular portion 41 and the protective ring 42, and regularly and angularly distributed around the longitudinal axis A, in the example shown. In an embodiment not shown, the three legs can be distributed around the longitudinal axis to form a U shape.

The proximal end 43a of each leg 43 is linked to the tubular portion 41 by means of a proximal hinge 44, and the distal end 43b of each leg 43 is linked to the protective ring 42 by means of a distal hinge 45. Each leg 43 is further provided with an intermediate hinge 46 dividing the length of said leg 43 in a proximal segment 47 and a distal segment 48. As appears from FIGS. 10 and 11, for example when a force is exerted on the protective ring 42 in the proximal direction with the tubular portion 41 being maintained in a fixed position, the proximal hinge 44 allows the proximal segment 47 of the leg 43 to pivot with respect to the tubular portion 41 in the radial outward direction, the distal hinge 45 allows the distal segment 48 of the leg 43 to pivot with respect to the protective ring 42 in the radial outward direction, and the intermediate hinge 46 allows the proximal and distal segments (47, 48) to pivot with respect to each other, and the protective ring 42 is translated in the proximal direction along the longitudinal axis A. As a consequence, the foldable member 40 is capable of going from an unfolded configuration, as shown on FIG. 4, to a fully folded configuration, as shown on FIG. 11, while going through intermediate folded configurations, as shown on FIG. 10. As such, the overall length of the foldable member 40, in other words the length of the member 40 from its proximal end 40a to its distal end 40b, measured along longitudinal axis A, and in particular the length of each leg 43, measured from its proximal end 43a to its distal end 43b along longitudinal axis A, is reduced when the foldable member 40, in particular each leg 43, goes from its unfolded configuration, as shown on FIG. 4, to an intermediate folded configuration, as shown on FIG. 10, or to its fully folded configuration, as shown on FIG. 11.

With reference to FIGS. 1 and 2 and FIGS. 5 and 6, the proximal segment 47 of each leg 43 has a proximal end 47a and is further provided in the distal region of its outer wall with an outer projection 47b and with a groove 47c, the groove 47c being proximally spaced with respect to said outer projection 47b.

The operation of the needle assembly 1 and of the injection device 3 of the invention will now be described with respect to FIGS. 1-11 and 13.

As appears from the above description and as will be clear from the following description, in the needle assembly 1 and injection device 3 of the invention, the protective ring 42 is capable of moving in translation with respect to the needle hub 4 between a distal position, in which the protective ring 42 surrounds at least the distal tip 6 of the needle 5 and in which the needle safety system is in one of a storage condition (as shown on FIG. 1) or end-of-use condition (as shown on FIG. 13), and a proximal position, in which the protective ring 42 leaves said distal tip 6 uncovered and wherein the needle safety system is in a use condition, said protective ring 42 being movable in said proximal position between intermediate positions, as shown on FIG. 5, in which the needle 5 is partially inserted into an injection site (not shown), and a most proximal position, in which the needle 5 is fully inserted in the injection site and where an injection step may take place, as shown on FIG. 6: as such, FIG. 5 shows an intermediate condition of the needle assembly, in which the distal tip 6 of the needle 5 is uncovered, corresponding to the beginning of an insertion step of the needle 5 inside the injection site or alternatively to a misuse step of the injection device 3. On FIG. 6, the needle 5 is fully inserted in the injection site and the injection as such may be completed.

As appears also from FIGS. 4, 10 and 11, in the needle assembly 1 and injection device 3 of the invention, foldable means, the foldable member 40 in the example shown, are coupled to the protective ring 42 and to the needle hub 4, and are capable of going from an unfolded configuration, in which the protective ring 42 is in its distal position, as shown on FIG. 4, to a fully folded configuration, in which the protective ring 42 is in its most proximal position, as shown on FIG. 11. Between its most proximal position and its distal position, the protective ring 42 may be in an intermediate position, corresponding to an intermediate folded configuration of the foldable means, as shown on FIG. 10.

Moreover, in the needle assembly 1 and injection device 3 of the invention, biasing means, the helical spring 30 in the example shown, are capable of expanding from a stressed state to a rest state for urging the foldable means, the foldable member 40 in the example shown, from their fully folded configuration to their unfolded configuration at the end of the injection step.

The user is provided with the needle assembly 1 of the invention in a storage condition of the needle assembly 1, corresponding to a condition of the needle assembly before use, as shown on FIGS. 1 and 2. In the example shown, the needle hub 4 is a part of the container 2 intended to receive the product to be injected in an injection site (not shown) via the injection device 3 formed by the needle assembly 1 and the container 2. On these figures, the stopper intended to close the proximal end of the container once it is filled and the piston rod intended to move the stopper distally so as to perform injection, are not shown.

With reference to FIGS. 1 and 2, the needle hub 4 is received within the tubular portion 41 of the foldable member 40. The tubular portion 41 as such does not constitute a foldable part of the foldable member 40 and this tubular portion 41 is fixed in translation with respect to the needle hub 4 by means of its proximal inner rim 41*a* being engaged in the circular groove 7 of the needle hub 4. In this storage condition of the needle safety system, the foldable member 40 is in its unfolded configuration, as shown on FIG. 4, and the protective ring 42 is therefore in its distal position, thus surrounding and protecting the distal tip 6 of the needle 5.

In embodiments not shown, the needle hub of the needle assembly is not a part of the container but an independent piece having the needle 5 fixed thereon. In such embodiments, the needle hub may be received within the tubular portion of the foldable member, or the needle hub and the tubular portion may form a single piece. In both cases, the needle hub is fixed in translation with respect to the distal end of the container.

Still with reference to FIGS. 1 and 2, the tubular portion 41 of the foldable member 40 is received within the fixed ring 10, this tubular portion 41 being fixed in translation with respect to the fixed ring 10 by means of its window 41*b* engaging the circular ridge 11 of the fixed ring 10. As a consequence, the fixed ring 10 is fixed in translation with respect to the needle hub 4, by the intermediate of the tubular portion 41. The mobile ring 20 is partially received in the fixed ring 10, said mobile ring 20 being coupled to the fixed ring 10 by means of the helical spring 30. As already mentioned above, the proximal end 30*a* of the helical spring 30 bears on the proximal radial abutment surface formed by the circular ridge 11 of the fixed ring 10, and the distal end 30*b* of the helical spring 30 bears on the distal radial abutment surface formed by the circular ridge 21 of the mobile ring 20. As appears from FIG. 2 and from FIG. 7, in this storage condition of the needle assembly 1, the helical spring 30 is maintained in an intermediate stressed state by means of peg 22 of mobile ring 20 being engaged in the distal end 14*b* of the side track 14 of the cam 12 of the fixed ring 10, said distal end 14*b* forming a recess in which said peg 22 is blocked, said peg 22 being therefore in a locked state. The peg 22 and the distal closed end 14*b* of the side track 14 therefore form retaining means for maintaining the helical spring 30 in its intermediate stressed state in the storage condition of the needle assembly 1.

In the example shown, the peg 22 is located on the mobile ring 20. In embodiments not shown, the peg could be located on the foldable means 40.

In the storage condition of the needle assembly 1 as shown on FIG. 1, the mobile ring 20 is therefore blocked in distal translation with respect to the fixed ring 10. In addition, as will appear from the following description, it is limitedly movable in proximal translation and in rotation with respect to the fixed ring 10, said proximal translation and rotation being conditioned to the cooperation of the peg 22 within the cam 12.

When the user is ready to perform the injection, he grasps the injection device 3, for example by the container 2, and applies the distal end of the injection device 3, in other words the distal end of the protective ring 42 on the skin of the patient (not shown). For clarity's sake, on the figures of the present application, the product to be injected, the stopper and the piston rod are not shown. Once the protective ring 42 is applied on the skin of the patient, the user applies a distal force on the proximal end of the injection device 3, thereby causing the insertion of the needle 5 in the skin of the patient. Such a movement causes the proximal movement of the protective ring 42 with respect to the needle hub 4, as shown on FIG. 5. The protective ring 42 being linked to the legs 43 by means of distal hinges 45, the distal segments 48 are caused to pivot with respect to the protective ring 42, the proximal segments 47 are caused to pivot with respect to the distal segments 48 via intermediate hinges 46, and to pivot with respect to the tubular portion 41 and to the needle hub 4 via proximal hinges 44. The foldable member 40 is caused to move to an intermediate folded configuration, as shown on FIGS. 5 and 10.

During this movement, the proximal segment 47 of each leg 43 has been caused to expand radially outwardly as shown on FIG. 5, and more precisely on FIG. 8. This has caused the distal end 47*a* of the proximal segment 47 to come in abutment against the distal end 20*b* of the mobile ring 20 and to push said distal end 20*b* in the proximal direction, as shown on FIG. 8. The proximal movement of the mobile ring 20 causes the peg 22 to move within the cam 12, and in particular in side track 14, therefore acting as a guiding means of peg 22 so as to cause rotation and proximal translation of the mobile ring 20 with respect to the fixed ring 10. As a consequence, peg 22 escapes from side track 14 and enters longitudinal track 13, as shown on FIG. 8, said peg 22 being therefore in a free state. In the free state of the peg 22 as shown on FIG. 8, the retaining means of the helical spring are therefore released, the proximal end 47*a* of the proximal segment 47 and the mobile ring 20 having acted as deactivating means of these retaining means. Indeed, as soon as the protective ring 42 is moved on at least 2 mm, preferably at least 5 mm, in the proximal direction, the distal end 47*a* of the proximal segment 47 comes in abutment against the distal end 20*b* of the mobile ring 20, pushes the distal end 20*b* in the proximal direction leading indirectly via the movement of the peg 22 to the release of the retaining means of the helical spring 30.

Anyway, thanks to the user continuing exerting a distal pressure on the injection device 3, the peg 22 is not yet allowed to travel in the longitudinal track 13 in a distal direction and the helical spring 30 is therefore maintained in an intermediate stressed state.

The user then carries on the insertion step of the needle 5 and continues to exert a distal pressure on the injection device 3 in order to fully insert the needle 5 up to the adequate injection site (not shown). On FIG. 6 is shown the needle assembly 1 and injection device 3 of the invention, once the needle 5 is fully inserted up to the injection site and the injection step as such may properly take place. The needle assembly 1 and the injection device 3 are therefore in a use condition, in which the needle 5 is fully inserted and the injection device 3 is ready for injection step. As appears from FIG. 6, the protective ring 42 has continued to move in the proximal direction and has now reached its most proximal position. During this movement, the foldable member 40 has left its intermediate folded configuration shown on FIG. 10 in order to reach its fully folded configuration shown on FIG. 11. This has caused the proximal segment 47 to reach a nearly perpendicular position with respect to the longitudinal axis A, as shown on FIG. 6. As a consequence, as shown on FIG. 9, the proximal end 47a of the proximal segment 47 has kept on pushing the mobile ring 20 in proximal direction via its distal end 20b. This has caused the peg 22 to move in the longitudinal track 13 in the proximal direction up to the proximal end 13a of said longitudinal track 13a. The peg 22 coming in abutment against the closed proximal end 13a of the longitudinal track 13 forms therefore an indication to the user that the needle 5 is fully inserted in the injection site and that the injection step may be started. This movement has also exerted an additional compression on the helical spring 30 and has therefore caused the helical spring 30 to move from its intermediate stressed state to its stressed state, said stressed state corresponding to the most stressed state reachable by the helical spring in the example shown.

As a consequence, in the use condition of the needle assembly 1, with the needle 5 fully inserted and the device 3 ready for injection step, as shown on FIGS. 6, 9 and 11, the user may perform the injection as such. This step is not shown on the figures as it consists in expelling the product from the container by pushing distally on the piston rod, said operations having no interaction with the needle assembly of the invention.

During the injection step, the user continues applying enough distal pressure on the injection device 3 and thus on needle assembly 1, so that the peg 22 remains in its position shown on FIG. 9, in abutment against closed distal end 13a of longitudinal track 13 of cam 12, the helical spring 30 being in its stressed state.

Once the injection step is over, the user withdraws the injection device 3, thereby removing the needle 5 from the injection site and relieving his distal pressure on the injection device 3. The peg 22 is free to move in the distal direction in the longitudinal track 13 and no more acts as retaining means of the helical spring 30 in its stressed state. As a consequence, the helical spring 30 tends to reach its rest state and automatically expands, thereby pushing the mobile ring 20 in the distal direction, said peg 22 escaping definitely the cam 12 and the fixed ring 10 by exiting the longitudinal track 13 by its open distal end 13b (see FIG. 9). The distal movement of the mobile ring 20 pushed by the helical spring 30 causes the distal end 20b of the mobile ring 20 to push distally the proximal end 47a of the proximal segment 47 which thus pivots back radially inwardly, thereby urging the whole foldable member 40 to its unfolded configuration as shown on FIG. 13. The protective ring 42 is back to its distal position, in which it surrounds the distal tip 6 of the needle 5 and protects the user from accidental needlestick injuries. The biasing means, the helical spring 30 in the example shown, therefore forms automatic means for triggering the needle safety system of the needle assembly 1 of the invention when the needle is removed from the injection site at the end of the injection step, with no additional operation requested from the user, other than withdrawing the injection device 3 from the injection site.

In the end-of-use condition of the needle assembly 1 and injection device 3 as shown on FIG. 13, the mobile ring 20 is in a distal position with respect to the needle hub 4 and the fixed ring 10, in which it receives at least part of the foldable member 40. In particular, as appears from FIG. 13, the circular ridge 21 of the mobile ring 20 is now engaged in the window 47c of the proximal segment 47 of the leg 43 of the foldable member 40, and the distal end 20b of the mobile ring 20 is in abutment against the outer projection 47b of said proximal segment 47. As a consequence, even if a user applies a proximal force on the protective ring 42, the foldable member 40 is not allowed to move towards an intermediate folded configuration. The mobile ring 20, the circular ridge 21, the window 47c, the distal end 20b and the outer projection 47b form locking means of the foldable member in its unfolded configuration, in said end-of-use condition of the needle assembly 1.

In addition, the fact that the foldable member is locked in its unfolded configuration by a mobile ring such as the mobile ring 20 described above, at least partially facing a distal area of the proximal segment, prevents a user from manually trying to fold again the foldable member for example by directly grasping the legs 43 and attempting at moving them outwardly radially in a view of using the needle assembly again. In particular, the fact that the circular ridge 21 of the mobile ring 20 is engaged in the window 47c of the proximal segment 47 of the leg 43 of the foldable member 40 provides a double lock as not only the foldable member may not be folded again, but the mobile ring itself may not be removed from its position.

The presence of at least a mobile ring 20 as part of the locking means of the foldable member as shown in the present invention allows the locking means to be both automatically triggered and unreleasable once triggered: indeed, thanks to the safety system of the needle assembly of the invention, no additional step is required from the user in order to trigger the locking means and the user has no way of releasing or unlocking said locking means in the end-of-use condition of the needle assembly.

On FIG. 14, is shown a cap intended to be mounted on the needle assembly 1 when the needle assembly 1 is in a storage condition, as shown on FIG. 1, for example for transportation purposes. The protective cap 50 is dimensioned so as to surround the needle assembly 1. The protective cap 50 has the global shape of a tube open at its proximal end 50a and closed at its distal end 50b. The protective cap 50 comprises an elastomeric part 51 extending proximally from an inner face 52a of a transversal wall 52 closing its distal end 50b. As appears from FIG. 14, the elastomeric part 51 is dimensioned so as to be able to be received within the protective ring 42 when the protective cap 50 is mounted on the needle assembly 1, and the distal tip 6 of the needle 5 is intended to be received in the elastomeric part 51. The elastomeric part 51 can be in different materials, in rubber for example or preferably in an elastomeric material, like thermoplastic elastomers (TPE) as styrenic block copolymers, polyolefin blends, elastomeric alloys, thermoplastic polyurethanes, thermoplastic copolyester or thermoplastic polyamides.

The protective cap 50 is further provided on a certain length of its inner wall with a longitudinal ridge 53, said longitudinal ridge having a proximal end 53a. When the protective cap 50 is mounted on the needle assembly 1 of FIG. 1, the proximal end 53a of the longitudinal ridge 53 is directed towards the open distal end 13a of the longitudinal track 13 of the cam 12, so that the proximal region of the longitudinal ridge 53 is engaged in the longitudinal track 13 during storage and/or transportation of the needle assembly 1 provided with said protective cap 50, said longitudinal ridge 53 preventing said peg 22 from escaping from said side track 14.

The risk that the biasing means of the needle assembly 1, the helical spring 30 in the example shown, be accidentally triggered is therefore avoided. The longitudinal ridge 53 of the protective cap therefore forms securing means for preventing the biasing means from being accidentally triggered.

On the example shown on these Figures, the foldable member 40 comprises three legs 43. Such an embodiment allows obtaining a good stability of the foldable member 40 during its changes of configurations. Nevertheless, in other embodiments, the foldable member 40 may comprise only one leg or only two legs opposite each other with respect to the needle. The foldable member may also comprise four or more legs, distributed around the needle.

Figure 12:
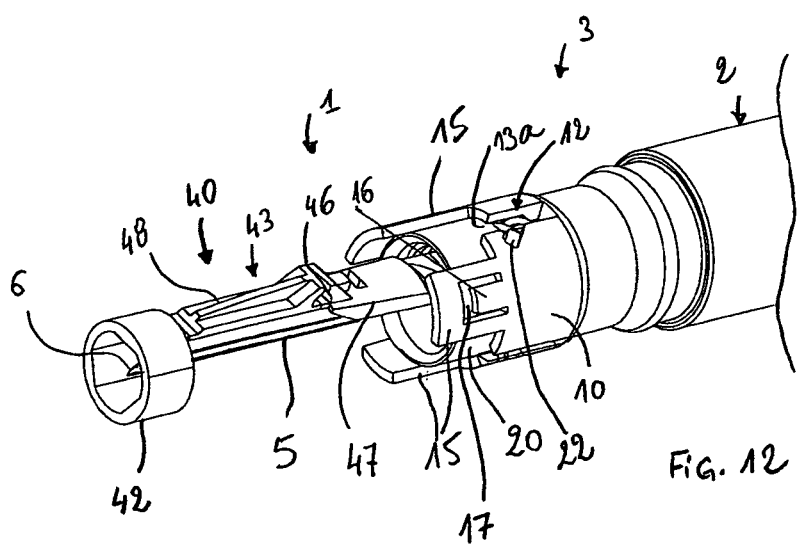
FIG. 12 is a partial perspective view of another embodiment of the needle assembly and injection device of the invention, in the storage condition of the needle assembly.

With reference to FIGS. 12 and 16, is shown another embodiment of the needle assembly 1 of the invention, in which the foldable member 40 comprises only one leg 43, parallel to the needle 5. The references designating the same elements as in FIGS. 1-11 and 13 have been maintained on FIGS. 12 and 16. The single leg 43 of the embodiment on these Figures functions exactly in the same manner as the legs 43 of FIGS. 1-11 and 13 and it will not be described again herein. On FIG. 12, the needle assembly 1 is in its storage condition, with the peg 22 in its locked state. The fixed ring 10 of this embodiment is further provided with tongues 15, three in the example shown, extending in the proximal direction. These tongues 15 are circumferentially spaced from the open end 13*a* of the longitudinal track 13 of cams 12, and from the leg 43, so as to allow the proximal segment 47 to expand radially outwardly when the foldable member 40 moves to its folded configuration. These tongues 15 provide protection of the helical spring 30 when it is in its rest state in the end-of-use condition of the needle assembly 1, as shown on FIG. 16. In particular, the tongues 15 act as protection means of the helical spring 30 in its rest state so as to prevent access to said helical spring 30 to a user. The tongues 15 are further provided with fingers 16 radially flexible in windows 17 provided in tongues 15, these fingers 16 being capable of engaging an outer rim 23 provided at the proximal end of the mobile ring 20 so that the fixed ring 10 and the mobile ring 20 form a continuous protective wall of the helical spring 30 in the end-of-use condition of the needle assembly 1, as shown on FIG. 16. In alternative embodiments, as shown on FIG. 15, for which the references designating the same elements as on FIGS. 12 and 16 have been maintained, and where the needle assembly 1 is in its end of use condition, the tongues 15 do not include such windows and flexible fingers, and the mobile ring 20 is not provided with such an outer rim, the fixed ring 10 and the mobile ring 20 nevertheless forming a continuous protective wall of the helical spring 30 in the end-of-use condition of the needle assembly 1. The alternative embodiments of the fixed ring 10 and mobile ring 20 may also be combined with the embodiment of FIGS. 1-11 and 13, where the foldable member 40 comprises three legs 43. Such protection obtained by the tongues 15 of the fixed ring 10 may be required in order to avoid any voluntary unlocking of the safety system in the end-of-use condition. Indeed, with this embodiment of the fixed ring 10, the tongues 15 and the mobile ring 20 are at the same level along longitudinal axis A, thereby preventing any possibility to move the needle assembly 1 from an end-of use condition to a storage condition.

The needle assembly of the invention allows obtaining compact injection devices, occupying little volume and therefore easy to package and to store, even when these injection devices are prefilled with the product to be injected, the injection devices being in addition provided with an efficient needle safety system allowing the automatic triggering of the needle protection at the end of injection or after a misuse of the injection device, with no additional operation requested from the user other than withdrawing the injection device from the injection site. In addition, the needle assembly of the invention may be provided with a double lock system allowing the locking means of the foldable means to be both automatically triggered and permanent once triggered: the needle assembly of the invention is therefore highly safe.

The invention claimed is:

1. A needle assembly for use with a container, comprising:
   i) a needle hub having a needle fixed thereon, said needle having a distal tip and
   ii) a needle safety system comprising:
      a protective ring capable of moving in translation with respect to said needle hub between a distal position, in which said protective ring surrounds at least the distal tip of said needle and in which said needle assembly is in one of a storage condition or end-of-use condition, and a proximal position, in which said protective ring leaves said distal tip uncovered and wherein said needle assembly is in a use condition, said protective ring being movable in said proximal position between intermediate positions in which the needle is partially inserted into an injection site and a most proximal position, in which the needle is fully inserted into said injection site;
      a mobile ring coupled to said needle hub and movable in translation with respect to said needle hub between a proximal position and a distal position;
      a foldable element coupled to said protective ring and to said needle hub, capable of going from an unfolded configuration, in which said protective ring is in its distal position, to a fully folded configuration, in which said protective ring is in its most proximal, position;
      a biasing element coupling said needle hub and said mobile ring, said biasing element capable of expanding from a stressed state to a rest state urging said foldable element from the fully folded configuration to the unfolded configuration when the needle is removed from the injection site;
      a retaining mechanism for maintaining said biasing element in an intermediate stressed state at least in the storage condition of the needle assembly;
      a deactivating mechanism for releasing said retaining mechanism during the insertion step of the needle; and
      a locking mechanism for maintaining said foldable element in the unfolded configuration in the end-of-use condition of said needle assembly, wherein said mobile ring forms at least part of said locking mechanism.

2. The needle assembly according to claim 1, wherein said mobile ring forms at least part of said retaining mechanism and said deactivating mechanism when said mobile ring is in said proximal position, and wherein said mobile ring forms at least part of said locking mechanism when said mobile ring is in said distal position.

3. The needle assembly according to claim 1, wherein said safety system further comprises:
   a fixed ring at least partially receiving said needle hub, and fixed in translation with respect to said needle hub, wherein said
   mobile ring is coupled to said fixed ring by said biasing element, and capable of being at least partially received within said fixed ring.

4. The needle assembly according to claim 3, wherein said fixed ring is provided with a proximal radial abutment surface and said mobile ring is provided with a distal radial abutment surface, said biasing element is a helical spring located between said fixed ring and said mobile ring so that the distal end of said helical spring bears on said distal radial abutment surface and the proximal end of said helical spring bears on the proximal radial abutment surface, and said retaining mechanism comprising a cam provided with a recess, said cam being located on one of said fixed ring and mobile ring, and a peg located on the other one of said fixed ring and mobile ring, said peg being capable of moving within said cam between a locked state in which said needle assembly is in its the storage condition and said peg is engaged in said recess, said helical spring being in its intermediate stressed state, and a free state in which said peg is disengaged from said recess after activation of said deactivating mechanism, said needle assembly being then in one of its use or end-of-use conditions.

5. The needle assembly according to claim 1, wherein at least part of said deactivating mechanism is located on said foldable element, said deactivating mechanism is activated when said foldable element is in the fully folded configuration.

6. The needle assembly according to claim 1, wherein said foldable element comprises at least one leg having a proximal end pivotally coupled to said needle hub, and a distal end pivotally coupled to said protective ring, said leg being provided with a hinge dividing a length of said leg in a proximal segment and a distal segment, said proximal and distal segments being aligned on each other and parallel to said needle in the unfolded configuration of said foldable element, said proximal and distal segments pivoting about said hinge and extending radially outwardly in the fully folded configuration of said foldable element.

7. The needle assembly according to claim 6, wherein said foldable element comprises at least two legs, the two legs being opposite each other with respect to said needle.

8. The needle assembly according to claim 6, wherein said foldable element comprises at least three legs, said three legs being regularly angularly distributed around said needle.

9. The needle assembly according to claim 4, wherein said cam being located on said fixed ring, said cam comprising a longitudinal track open at a distal end and closed at a proximal end, and a side track extending circumferentially and distally from a point of said longitudinal cam to a closed end, said side track forming said recess, said peg is located on said mobile ring and is disengageable from said side track by proximal translation and rotation of said mobile ring with respect to said fixed ring, said deactivating mechanism comprising at least a part of said proximal segments, said part of said proximal segments coming in abutment on a distal end of said mobile ring when said foldable element goes from the unfolded configuration to the fully folded configuration and said proximal segments extend radially outwardly, said part of proximal segments thereby pushing said mobile ring in the proximal direction, the movement of said peg in said side track thereby causing rotation of said mobile ring with respect to said fixed ring, thus disengaging said peg from said recess of said cam.

10. The needle assembly according to claim 4, wherein said retaining mechanism comprises three cams and three pegs, each cam cooperating with a corresponding peg, said cams being regularly angularly distributed along a circumference of said fixed ring, said corresponding pegs being regularly angularly distributed along a circumference of said mobile ring.

11. The needle assembly according to claim 2, wherein said locking mechanism comprises a groove located in a distal area of an outer wall of said proximal segment, and a radial rim located on an inner wall of said mobile ring, said radial rim being engaged in said groove in the end-of-use condition of said needle assembly, so as to prevent said hinge from allowing said proximal segment to pivot with respect to said distal segment.

12. The needle assembly according to claim 1, further comprising at least one protection element for preventing access to the biasing element in the end of use condition of the needle assembly.

13. The needle assembly according to claim 9, further comprising a protective cap intended to be mounted on said needle assembly when said needle assembly is in its storage condition, said protective cap being dimensioned so as to surround said needle assembly when it is mounted on said needle assembly.

14. The needle assembly according to claim 13, wherein said protective cap comprises an elastomeric part extending proximally from an inner face of a distal transversal wall of said cap, said elastomeric part being received within said protective ring and receiving the distal tip of said needle when said protective cap is mounted on said needle assembly.

15. The needle assembly according to claim 13, wherein said protective cap further comprises at least one securing element for preventing said biasing element to be accidentally triggered during storage of said needle assembly inside said protective cap.

16. The needle assembly according to claim 13, wherein the inner wall of said protective cap is provided with at least a longitudinal ridge, said longitudinal ridge being engaged in at least one of said longitudinal track of said cam when said protective cap is mounted on said needle assembly, said longitudinal ridge thereby preventing the corresponding peg from escaping from the recess formed by the side track in which said peg is engaged.

17. An injection device comprising a needle assembly for use with a container, comprising:

i) a needle hub having a needle fixed thereon, said needle having a distal tip, and ii) a needle safety system comprising:

a protective ring capable of moving in translation with respect to said needle hub between a distal position, in which said protective ring surrounds at least the distal tip of said needle and in which said needle assembly is in one of a storage condition or end-of-use condition, and a proximal position, in which said protective ring leaves said distal tip uncovered and wherein said needle assembly is in a use condition, said protective ring being movable in said proximal position between intermediate positions in which the needle is partially inserted into an injection site and a most proximal position, in which the needle is fully inserted into said injection site;

a foldable element coupled to said protective ring and to said needle hub, capable of going from an unfolded configuration, in which said protective ring is in its distal position, to a fully folded configuration, in which said protective ring is in its most proximal position;

a mobile ring coupled to said needle hub and movable in translation with respect to said needle hub between a proximal position and a distal position;

a biasing element coupling said needle hub and said mobile ring, said biasing element capable of expanding from a stressed state to a rest state urging said foldable element from the fully folded configuration to the unfolded configuration when the needle is removed from the injection site;

a retaining mechanism for maintaining said biasing element in an intermediate stressed state at least in the storage condition of the needle assembly, said mobile ring forms at least part of said retaining mechanism;

a deactivating mechanism for releasing said retaining mechanism retainer during the insertion step of the needle; and a container intended to be filled or filled with a product to be injected via said needle, wherein said needle hub is fixed to a distal end of said container.

18. The injection device according to claim 17, wherein said needle hub and said container are one single element.

19. The needle assembly according to claim 3, wherein said locking mechanism comprises a groove located in a distal area of an outer wall of said proximal segment, and a radial rim located on an inner wall of said mobile ring, said radial rim being engaged in said groove in the end-of-use condition of said needle assembly, so as to prevent said hinge from allowing said proximal segment to pivot with respect to said distal segment.

20. The needle assembly according to claim 1, further comprising a protective cap intended to be mounted on said needle assembly when said needle assembly is in its storage condition, said protective cap being dimensioned so as to surround said needle assembly when it is mounted on said needle assembly.

21. The needle assembly according to claim 20, wherein said protective cap comprises an elastomeric part extending proximally from an inner face of a distal transversal wall of said cap, said elastomeric part being received within said protective ring and receiving the distal tip of said needle when said protective cap is mounted on said needle assembly.

* * * * *

UNITED STATES PATENT AND TRADEMARK OFFICE
CERTIFICATE OF CORRECTION

PATENT NO. : 9,764,097 B2
APPLICATION NO. : 14/110851
DATED : September 19, 2017
INVENTOR(S) : Frédéric Perot et al.

Page 1 of 1

It is certified that error appears in the above-identified patent and that said Letters Patent is hereby corrected as shown below:

In the Claims

Column 17, Line 7, Claim 17, after "mechanism" delete "retainer"

Signed and Sealed this
Twenty-first Day of November, 2017

Joseph Matal
*Performing the Functions and Duties of the*
*Under Secretary of Commerce for Intellectual Property and*
*Director of the United States Patent and Trademark Office*